United States Patent
Ouchi et al.

(10) Patent No.: US 6,427,509 B1
(45) Date of Patent: Aug. 6, 2002

(54) PROCESS FOR PRODUCING A DISTAL END SUPPORT MEMBER OF AN ENDOSCOPIC TREATMENT TOOL

(75) Inventors: Teruo Ouchi, Saitama; Masaru Nagamine, Kagawa, both of (JP)

(73) Assignee: Asahi Kogaku Kogyo Kabusihi Kaisha, Tokyo (JP)

( * ) Notice: Subject to any disclaimer, the term of this patent is extended or adjusted under 35 U.S.C. 154(b) by 0 days.

(21) Appl. No.: 09/714,217

(22) Filed: Nov. 17, 2000

(30) Foreign Application Priority Data

Nov. 18, 1999 (JP) ............................................ 11-327785

(51) Int. Cl.7 .............................................. B21K 21/00
(52) U.S. Cl. ............................... 72/256; 72/334; 72/356
(58) Field of Search ......................... 72/256, 260, 333, 72/334, 356, 358, 359, 377

(56) References Cited

U.S. PATENT DOCUMENTS

| | | | | |
|---|---|---|---|---|
| 1,756,416 A | * | 4/1930 | Woodhead | 72/333 |
| 4,094,183 A | * | 6/1978 | Mettler | 72/359 |
| 4,662,047 A | * | 5/1987 | Berchem | 72/334 |
| 4,669,471 A | | 6/1987 | Hayashi | |
| 5,904,647 A | | 5/1999 | Ouchi et al. | |

FOREIGN PATENT DOCUMENTS

| | | | | |
|---|---|---|---|---|
| GB | 767854 | * | 2/1957 | 72/334 |
| GB | 2 067 445 | * | 7/1981 | 72/260 |

* cited by examiner

*Primary Examiner*—Lowell A. Larson
(74) *Attorney, Agent, or Firm*—Greenblum & Bernstein P.L.C.

(57) ABSTRACT

In a process by which a distal end support member of an endoscopic treatment tool that has a drive mechanism holding groove portion and a sheath coupling portion is fabricated, a drive mechanism holding groove portion is formed by forging that portion of a cylindrical metal stock which is closer to its front end such that it is extruded along the longitudinal axis to form a slit of gap in the middle while the sheath coupling portion is formed by forging that portion of the metal stock which is closer to its rear end such that it is extruded in an annular shape in a direction opposite the first direction of extrusion.

10 Claims, 12 Drawing Sheets

PROCESS FOR PRODUCING A DISTAL END SUPPORT MEMBER OF AN ENDOSCOPIC TREATMENT TOOL

BACKGROUND OF THE INVENTION

The present invention relates to a process for producing a distal end support member of an endoscopic treatment tool that is passed through a treatment tool insertion channel in an endoscope to be used for treatment in a body cavity.

FIG. 17 shows the distal end portion of endoscopic biopsy forceps which is one of the most commonly used endoscopic treatment tools. It comprises a flexible sheath 1, a manipulating wire 2 passed through the sheath 1 to be capable of moving back and forth along the longitudinal axis, a distal end support member 3 attached to the distal end of the sheath 1, and a pair of forceps cups 7 supported on the member 3 such that they can rotate about a support shaft 5 to open or close like beaks.

A groove 3a open toward the front end is formed in the front portion of the distal end support member 3. A drive mechanism 10 that is actuated by the manipulating wire 2 to drive the forceps cups 7 to open and close is held within the groove 3a which is in the form of a slit.

FIG. 18 shows the distal end support member 3 on its own. The rear portion 3A of the member 3 is formed like a tube into which the tip of the sheath 1 is to be inserted; as already mentioned, the groove 3a into which the drive mechanism 10 is to be held is formed in the front portion 3B of the member 3.

To fabricate the distal end support member 3, a rod-shaped workpiece must be subjected to at least two cutting operations, one being drilling from the back and the other being the formation of a groove in the front portion. In addition, the need to use a milling machine adds to the cost of parts fabrication.

SUMMARY OF THE INVENTION

An object, therefore, of the invention is to provide a process by which a distal end support member of an endoscopic treatment tool that has a drive mechanism holding groove portion and a sheath coupling portion can be fabricated at low cost.

According to the invention, a drive mechanism holding groove portion is formed by forging that portion of a cylindrical metal stock which is closer to its front end such that it is extruded along the longitudinal axis to form a slit of gap in the middle. A sheath coupling portion is formed by forging that portion of the metal stock which is closer to its rear end such that it is extruded in an annular shape in a direction opposite the first direction of extrusion. As a result, a distal end support member of an endoscopic treatment tool that has the drive mechanism holding groove portion and the sheath coupling portion can be fabricated at a very low cost.

As a preferred embodiment, the invention provides a process for producing a distal end support member of an endoscopic treatment tool which comprises a drive mechanism holding groove portion and a sheath coupling portion, the drive mechanism holding groove portion having a slit of gap formed to extend from its distal end so as to hold a distal end treatment member drive mechanism in a movable fashion and the sheath coupling portion being formed in an annular shape so that it can be coupled to the distal end of a sheath, characterized in that the drive mechanism holding groove portion is formed by forging that portion of a cylindrical metal stock which is closer to its front end such that it is extruded along the longitudinal axis to form a slit of gap in the middle whereas the sheath coupling portion is formed by forging that portion of the metal stock which is closer to its rear end such that it is extruded in an annular shape in a direction opposite the first direction of extrusion.

In order to extrude the sheath coupling portion by forging, the punch used to forge the drive mechanism holding groove portion may be replaced by a punch that defines an annular clearance from a die and which is used to perform forging in the same direction as the forging of the drive mechanism holding groove portion.

The punch and die that are used to forge the drive mechanism holding groove portion may have an annular clearance so that when the drive mechanism holding groove portion is extruded, the sheath coupling portion is simultaneously extruded between the punch and die.

A through-hole that crosses the slit of gap in the drive mechanism holding groove portion and which opens on both sides of the latter is pierced by extrusion by forging, provided that the side of the drive mechanism holding groove portion that first contacts a punch may be punched to make a hole and the resulting scrap is pushed forward until it contacts the other side of the drive mechanism holding groove portion and punches it to make another hole.

The present disclosure relates to the subject matter contained in Japanese patent application No. Hei. 11-327785 (filed on Nov. 18, 1999), which is expressly incorporated herein by reference in its entirety.

DESCRIPTION OF THE PREFERRED EMBODIMENT

Several modes for carrying out the invention are described below with reference to accompanying drawings.

Figure 1:
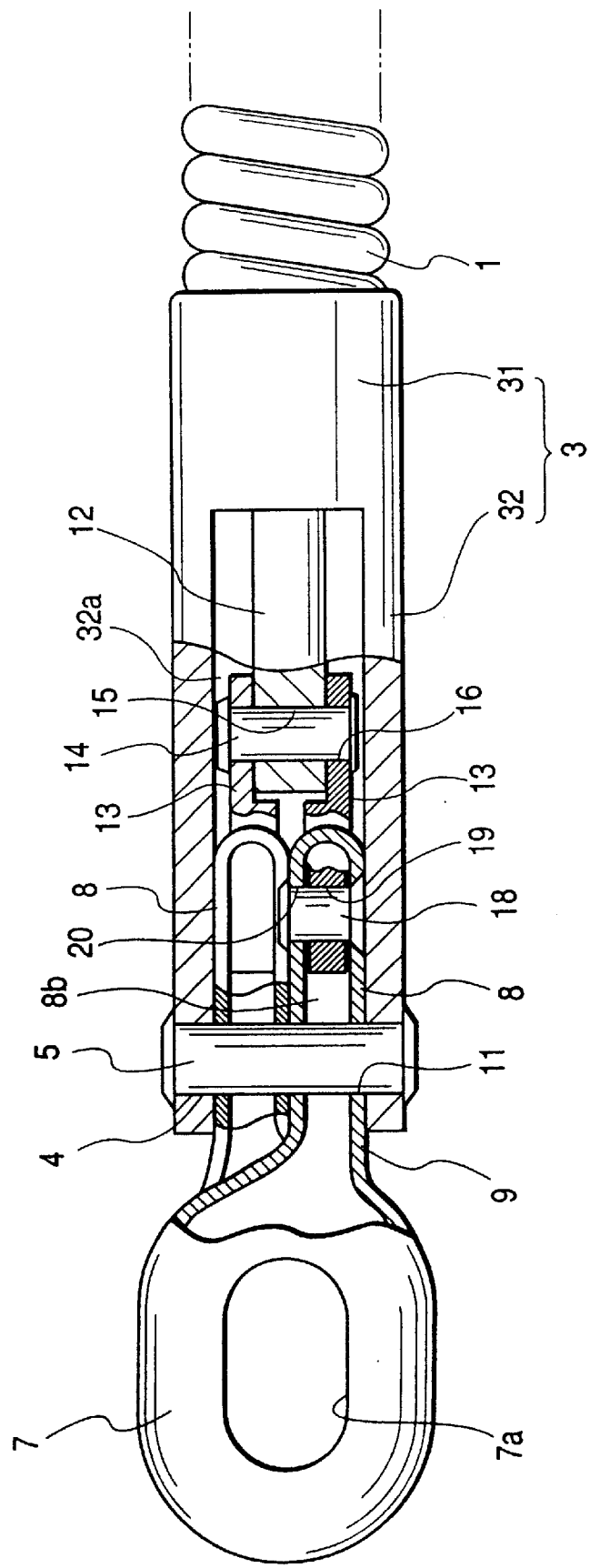
FIG. 1 is a plan view showing different sections of the distal end portion of endoscopic biopsy forceps in a closed state according to an embodiment of the invention.
Figure 2:
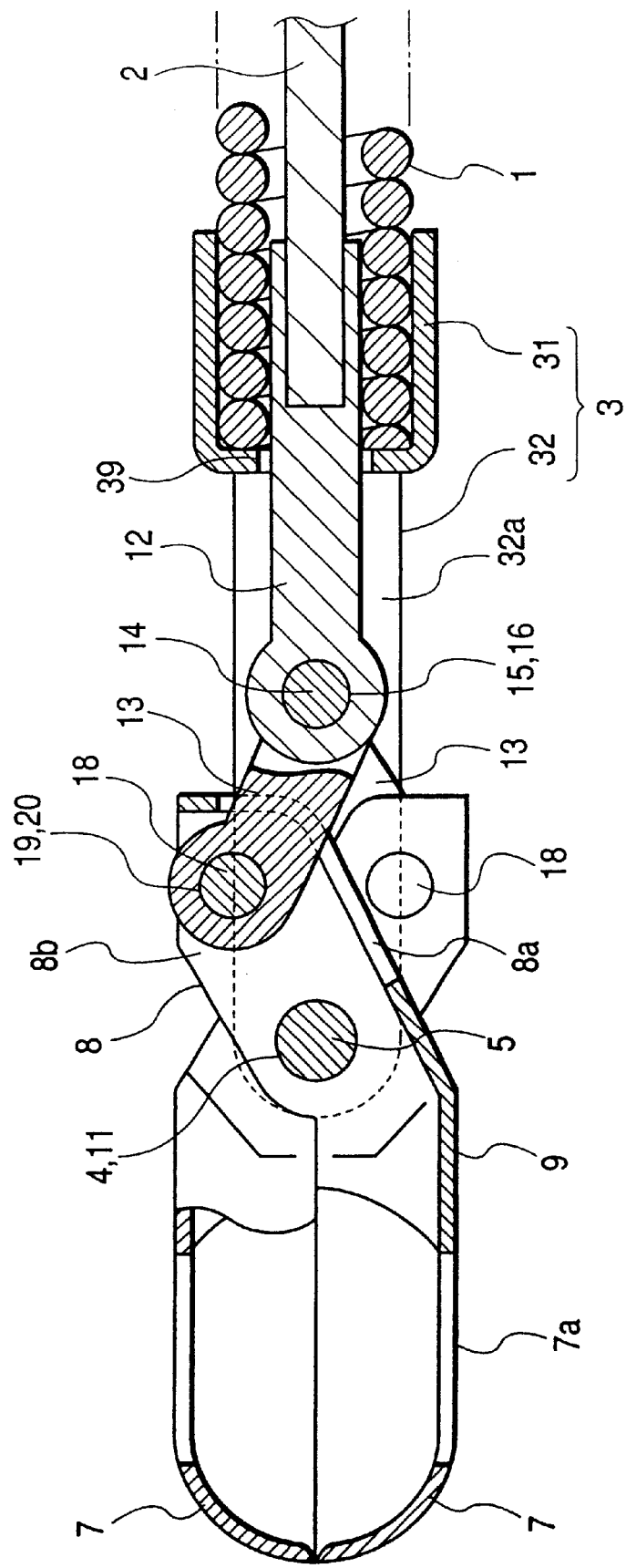
FIG. 2 is a side view showing different sections of the distal end portion of the same endoscopic biopsy forceps in a closed state.

FIG. 1 is a plan view showing, partly in section, the distal end portion of endoscopic biopsy forceps; FIG. 2 is a side view showing, partly in section, the same distal end portion. To save space, different sections are shown in one sheet.

A flexible sheath 1 to be passed into or removed from a forceps channel (not shown) in an endoscope is a tube in coil form made by winding a metal wire, typically a stainless steel wire, in close turns of a given diameter.

The sheath 1 may have other constructions; for example, the tube in coil form may be covered with a flexible tube to make the sheath 1. The sheath 1 has a length of about 1–2.5 m and a diameter of about 1.5–3 mm.

A manipulating wire 2 extends through the entire length of the sheath 1 in such a way that it can be moved back and forth along the longitudinal axis by manipulation from a manipulating section (not shown) connected to the basal end of the sheath 1.

Figure 6:
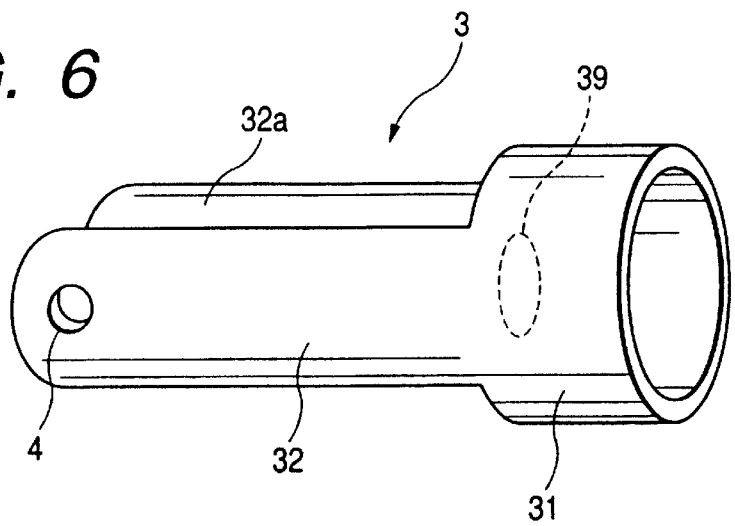
FIG. 6 is a perspective view showing the distal end support member of the same endoscopic biopsy forceps on its own.

A distal end support member 3 is securely coupled to the distal end of the sheath 1. As shown on its own in FIG. 6, the distal end support member 3 comprises a sheath coupling portion 31 formed in an annular shape so that it can be coupled to the distal end of the sheath 1 and a drive mechanism holding groove portion 32 having a slit of gap 32a formed to extend from its distal end so as to hold a distal end treatment member drive mechanism (e.g. drive levers 8 and link plates 13) in a movable fashion. Details of a process for producing the distal end support member 3 are given below.

The boundary between the sheath coupling portion 31 and the drive mechanism holding groove portion 32 has a hole 39 through which a wire coupling link 12 to be described later passes loosely along the central axis of the distal end support member 3.

The distal end support member 3 has a support shaft receiving hole 4 pierced through an area near its distal end (i.e., near the distal end of the drive mechanism holding groove portion 32) in a direction perpendicular to the longitudinal axis and a support shaft 5 is passed through the hole 4 and crimped at both ends.

Two sets of members which are integral assemblies of forceps cups 7 and drive levers 8 are pivotally supported on the support shaft 5. A pair of forceps cups 7, with the open sides facing each other, are provided to project forward from the distal end support member 3.

Figure 3:
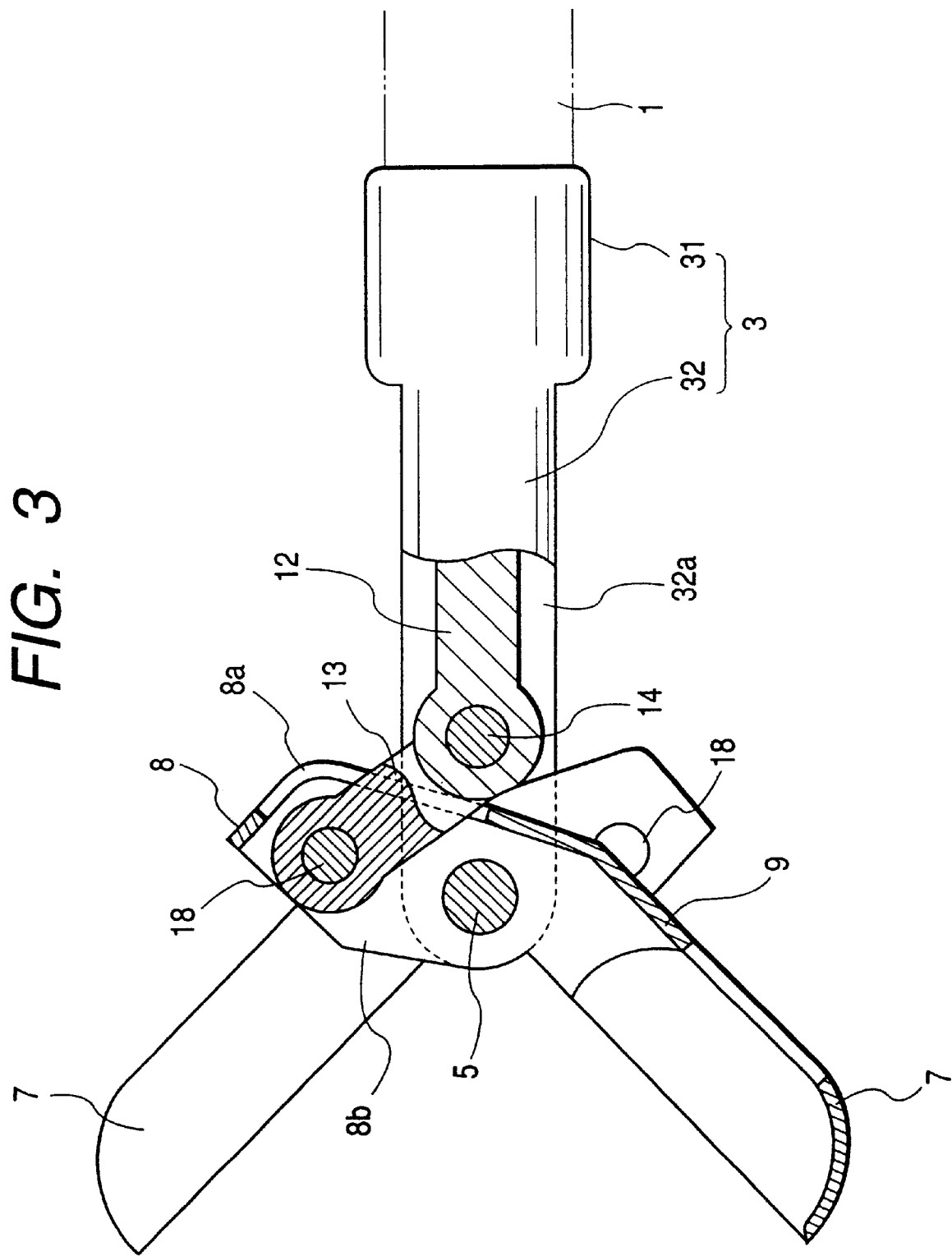
FIG. 3 is a side view showing, with part in section, the distal end portion of the same endoscopic biopsy forceps in an open state.

The drive levers 8 are accommodated in a movable fashion in the slit of gap 32a in the drive mechanism holding groove portion 32. The support shaft 5 held at both ends by the distal end support member 3 is passed through shaft holes 11 in the drive levers 8. When the drive levers 8 pivot about the support shaft 5, the forceps cups 7 integral with the drive levers 8 open and close like beaks. FIG. 3 shows the forceps cups 7 in the open state.

Figure 4:
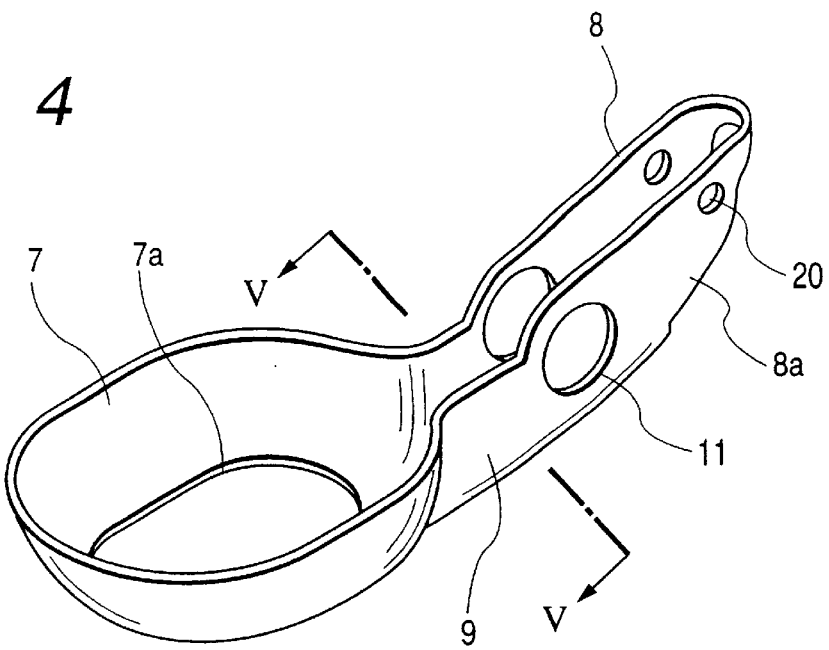
FIG. 4 is a perspective view showing a member of the same endoscopic biopsy forceps which is an integral combination of a forceps cup and a drive lever.

The forceps cups 7 and the drive levers 8 are formed from a single stainless steel sheet by pressing. FIG. 4 is a perspective view of forceps cup 7 and drive lever 8 in integral combination. A plan view of the combination is shown partly in section in FIG. 1.

The combination of forceps cup 7 and drive lever 8 is generally formed as a spoon with a short handle. The forceps cup 7 is a semi-oval member having an opening 7a in the back, with a blade formed along the edge of the open side.

Figure 5:
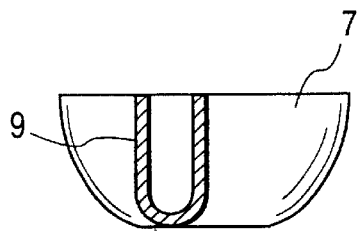
FIG. 5 is section V—V of FIG. 4 which shows the boundary between the forceps cup and the driver lever.

The boundary 9 between the forceps cup 7 and the drive lever 8 has a generally U-shaped cross section as shown in FIG. 5 which is section V—V of FIG. 4. The drive lever 8 also has a generally U-shaped cross section continuous from the boundary 9.

The distal end portion of the wire coupling link 12 in rod shape that is securely connected to the distal end of the manipulating wire 2 is positioned within the slit of gap 32a in the distal end support member 3. Two link plates 13 placed on opposite sides of the distal end portion of the wire coupling link 12 are pivotally connected to the wire coupling link 12 in an area near its distal end by means of a rivet 14.

The rivet 14 is loosely and rotatably passed through a hole 15 in the wire coupling link 12 and its opposite ends are retained in holes 16 in the two link plates 13 and crimped.

The hollow spaces 8b in the generally U-shaped drive levers 8 provide parallel grooves formed in a direction perpendicular to the longitudinal axis of the support shaft 5. The other end of each link plate 13 is inserted into the associated groove 8b and the link plates 13 are pivotally connected to the drive levers 8 by means of rivets 18 (pin-shaped members) each being retained by the associated drive lever 8 at both ends.

The two rivets 18 are rotatably and loosely fitted through holes 19 formed in the link plates 13 and each of them is retained at both ends by a hole 20 made in the associated drive lever 8. Shown by 8a is an opening made in the bottom of each drive lever 8 to allow for passage of the associated link plate 13.

Thus, the wire coupling link 12 and two each of the link plates 13 and drive levers 8 compose a link mechanism in the form of a pantograph. When the operator manipulates the wire 2 so that it is moved back and forth, the wire coupling link 12 is accordingly moved back and forth so that the drive levers 8 are allowed to pivot about the support shaft 5 by means of the link plates 13, causing the forceps cups 7 to open and close like beaks.

The link plates 13 are disposed within the parallel grooves 8*b* in the drive levers 8 and in engagement with rivets 18 each being received at opposite ends by the associated drive lever 8; hence, the link plates 13 and the drive levers 8 operate smoothly without skewing or leaning at the joints, allowing the forceps cups 7 to open and close in a positive manner. In a use mode, a mucosal tissue of a living body is held firmly between the two forceps cups 7 and torn off to be collected within the cups 7.

We next describe the process of the invention for fabricating the distal end support member 3 by forging.

FIGS. 7–15 show how the distal end support member 3 can be produced according to a first embodiment of the invention.

As shown, a die 100 has a stock receiving hole 101 which is open at the top such that a stock 3' in the form of a short cylindrical stainless steel rod is fitted from above with its longitudinal axis oriented perpendicularly.

Figure 7:
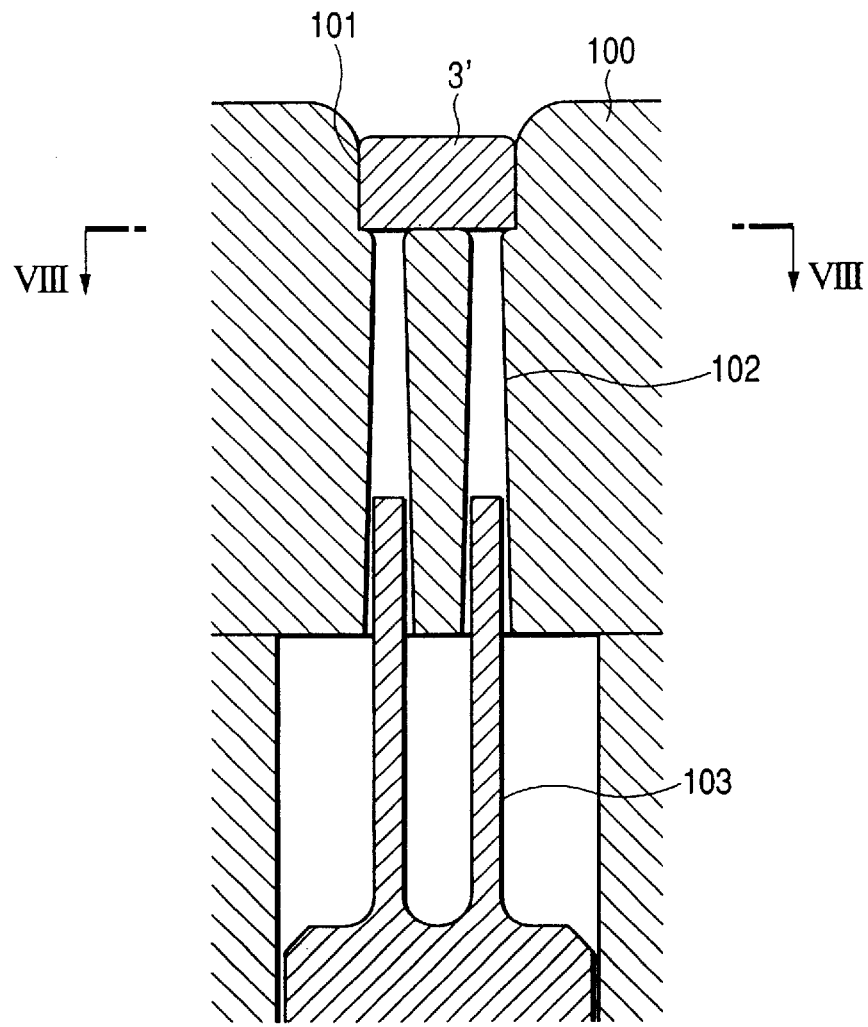
FIG. 7 is a front view showing in section a step in the process for producing a distal end support member of an endoscopic treatment tool according to the first embodiment of the invention.
Figure 8:
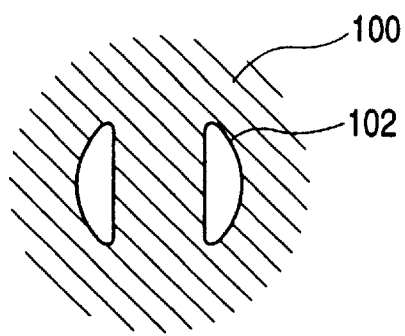
FIG. 8 is section VIII—VIII of FIG. 7.

As shown in FIG. 8 which is section VIII—VIII of FIG. 7, a pair of shaping holes 102 are pierced through the bottom of the stock receiving hole 101 such that the mouths of said holes 102 are conformal to the cross-sectional shape of the drive mechanism holding groove portion 32. As is clear from FIG. 7, the shaping holes 102 extend straight downward with a gradual increase in the cross-sectional area.

Ejector pins 103 for pushing the shaped article out of the die 100 are inserted into the shaping holes 102 from below in such a way that they are not detrimental to the purpose of ensuring the required length of the drive mechanism holding groove portion 32.

Figure 9:
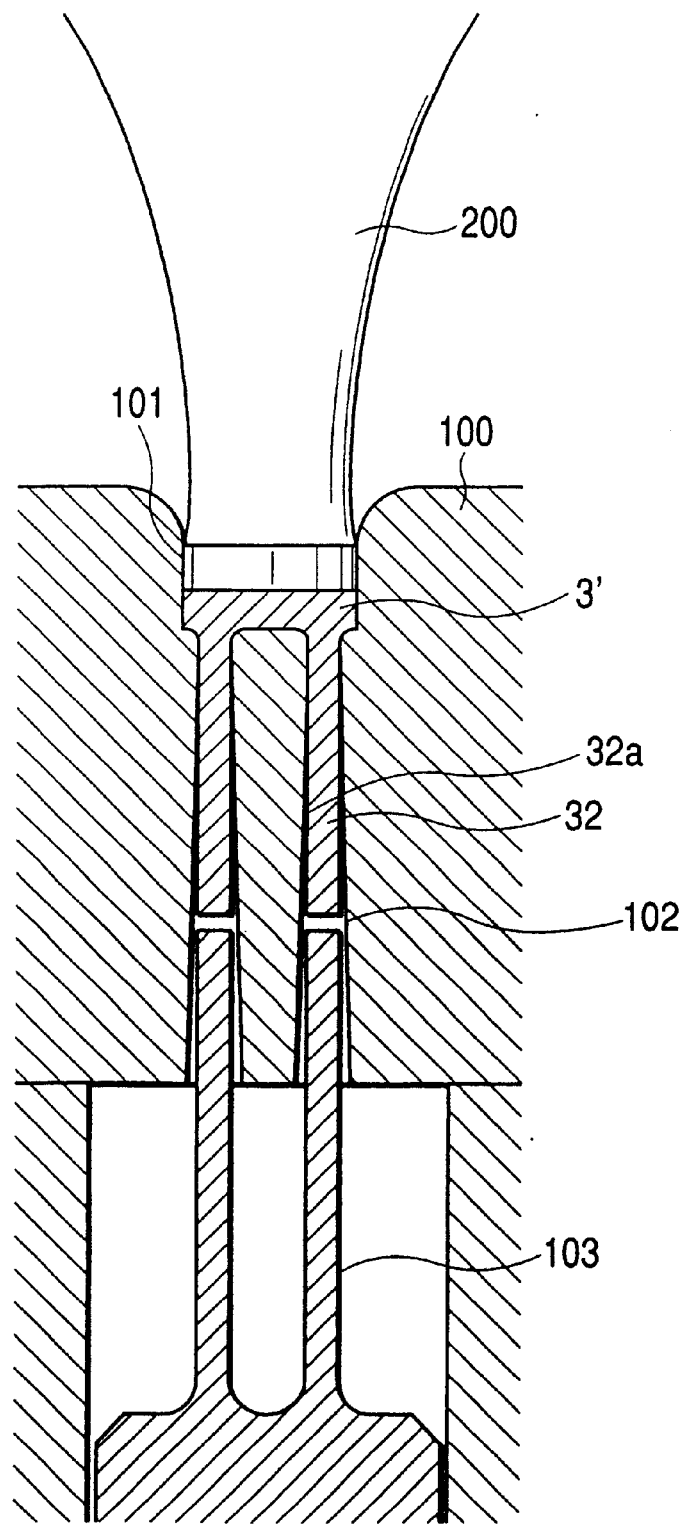
FIG. 9 is a front view showing in section a subsequent step in the process for producing a distal end support member of an endoscopic treatment tool according to the first embodiment of the invention.

In the embodiment under consideration, the stock 3' has a slightly larger diameter than the distal end support member 3. As shown in FIG. 9, the stock 3' fitted into the stock receiving hole 101 is pushed with a first punch 200 so that the lower part of the stock 3' is extruded into the shaping holes 102. The first punch 200 has such a diameter that it just fits within the die 100.

That part of the stock 3' which has been extruded into the shaping holes 102 has a cross-sectional shape that conforms to their mouths (see FIG. 8) and, as a result of this extrusion step, the drive mechanism holding groove portion 32 (and the slit of gap 32*a*) which constitute. the front part of the distal end support member 3 are shaped by forging.

Figure 10:
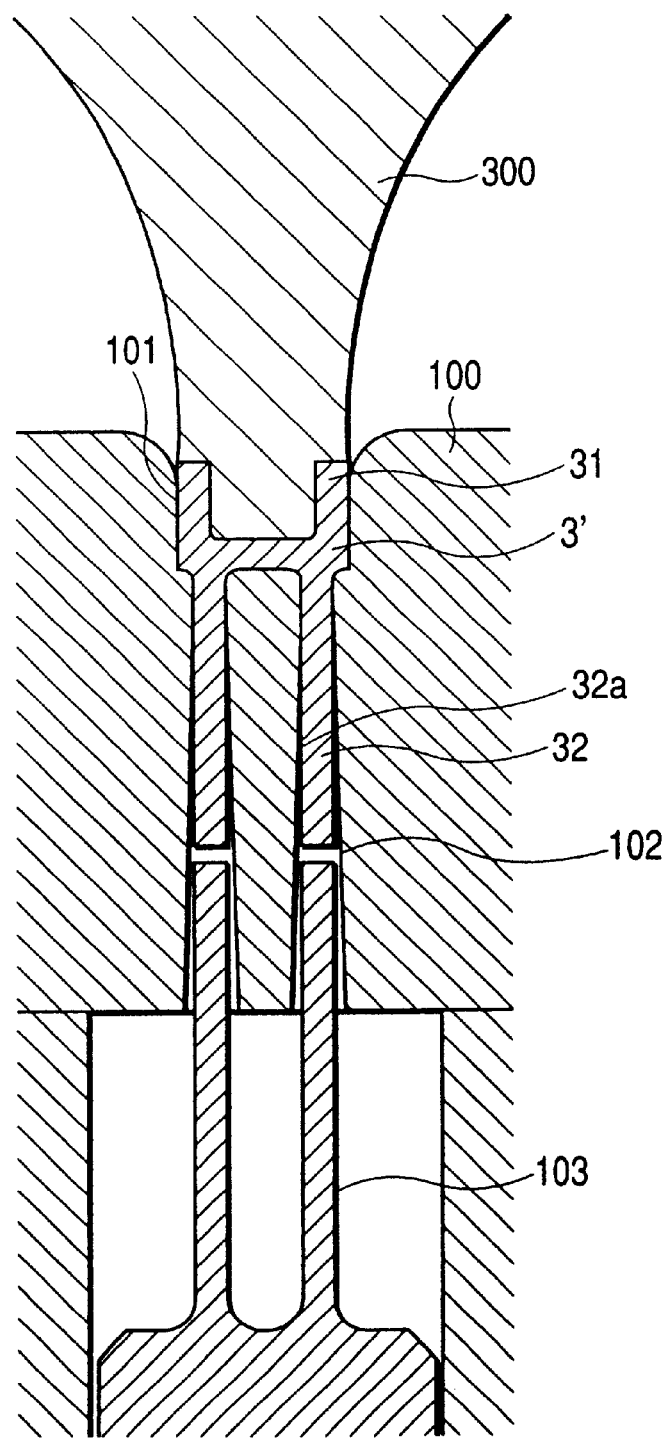
FIG. 10 is a front view showing in section a third step in the process for producing a distal end support member of an endoscopic treatment tool according to the first embodiment of the invention.

In the next step, as shown in FIG. 10, the first punch 200 is replaced by a second punch 300 having an annular clearance between its tip portion and the inner circumference of the stock receiving hole 101 in the die 100 and the stock 3' in the stock receiving hole 101 is pushed with this second punch.

As a result, the upper part of the stock 3' is pushed into the clearance between the tip portion of the second punch 300 and the stock receiving hole 101 in the die 100, whereupon the sheath coupling portion 31 which constitutes the rear part of the distal end support member 3 is formed by forging.

Figure 11:
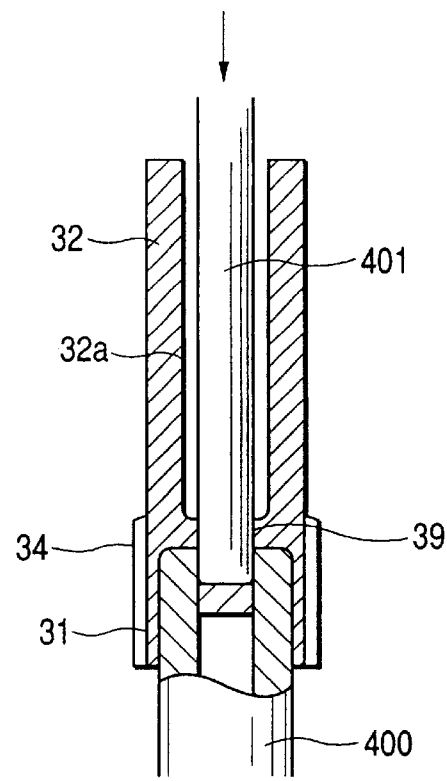
FIG. 11 is a front view showing in section a fourth step in the process for producing a distal end support member of an endoscopic treatment tool according to the first embodiment of the invention.

Once the sheath coupling portion 31 and the drive mechanism holding groove portion 32 have been formed, the shaped article is turned upside down and received by a cylindrical die 400 as shown in FIG. 11. Then, a first piercing punch 401 in rod shape is used to push out the part of the shaped article between the sheath coupling portion 31 and the drive mechanism holding groove portion 32 in a direction parallel to the longitudinal axis, whereupon the passage hole 39 is formed by forging.

Figure 12:
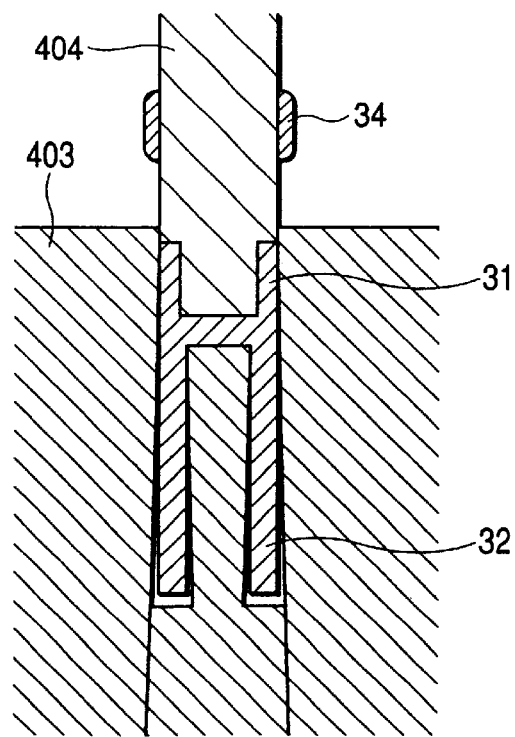
FIG. 12 is a front view showing in section a contour shaving step in the process for producing a distal end support member of an endoscopic treatment tool according to the first embodiment of the invention.

Then, as shown in FIG. 12, a flange portion 34 that protrudes from the outer circumference of the shaped article in its intermediate area is cut off by means of a contour shaving die 403 and punch 404, thereby producing a part that is identical in shape to the distal end support member 3 except that it has no support shaft receiving hole 4.

Figure 13:
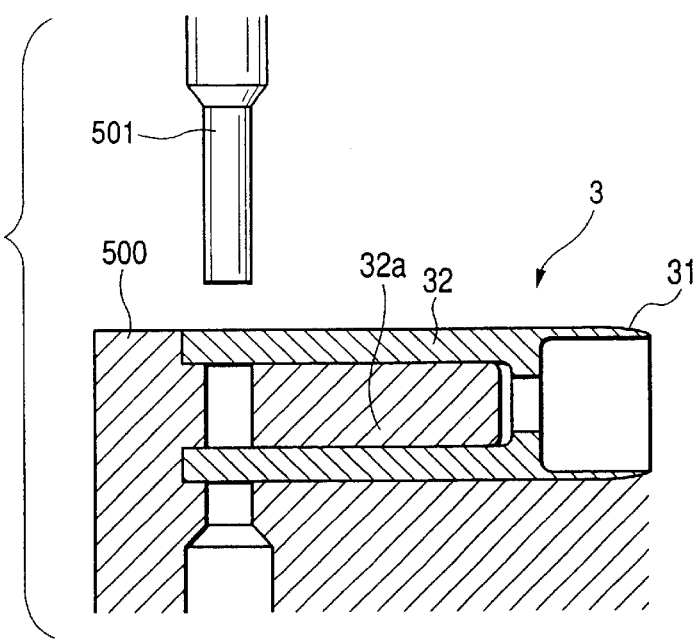
FIG. 13 is a side view showing in section a step in the stage of making a support shaft receiving hole in the process for producing a distal end support member of an endoscopic treatment tool according to the first embodiment of the invention.
Figure 14:
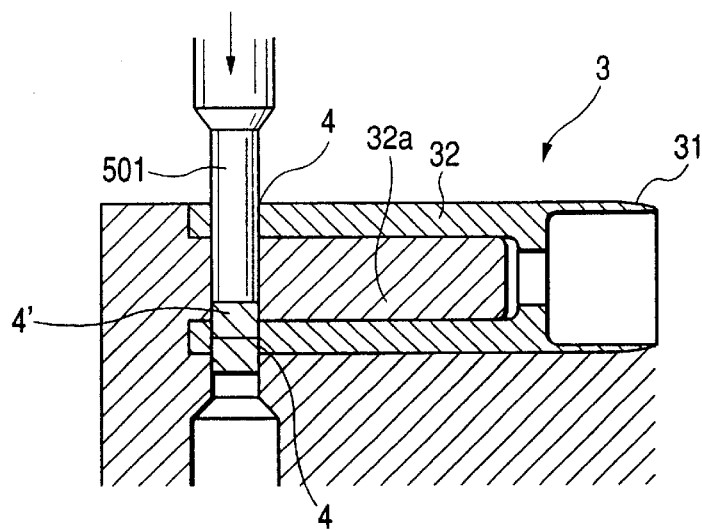
FIG. 14 is a side view showing in section a subsequent step in the stage of making a support shaft receiving hole in the process for producing a distal end support member of an endoscopic treatment tool according to the first embodiment of the invention.
Figure 15:
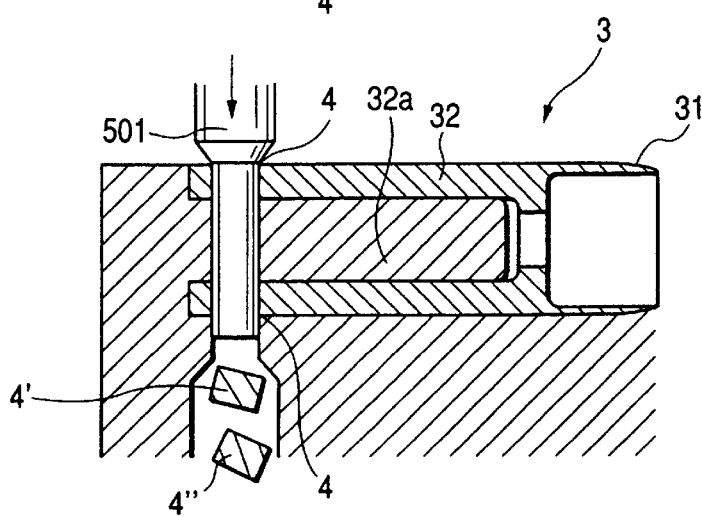
FIG. 15 is a side view showing in section a third step in the stage of making a support shaft receiving hole in the process for producing a distal end support member of an endoscopic treatment tool according to the first embodiment of the invention.

Finally, as shown in sequence in FIGS. 13–15, the part is placed laterally on a die 500 and punched with a second piercing punch 501 to form the support shaft receiving hole 4.

The support shaft receiving hole 4 is a through-hole that crosses the slit of gap 32*a* in the drive mechanism holding groove portion 32 and which opens on both sides of the latter. In order to form this hole, the side of the drive mechanism holding groove portion 32 that first contacts the second piercing punch 501 is punched to make a hole and the resulting scrap 41 is pushed forward so that it crosses the slit of gap 32*a* until it contacts the other side of the drive mechanism holding groove portion 32 and punches it to make another hole. Indicated by 4" is the scrap resulting from the second punching step. This punching operation is applicable to make other holes such as the shaft holes 11 in the forceps cups 7.

Figure 16:
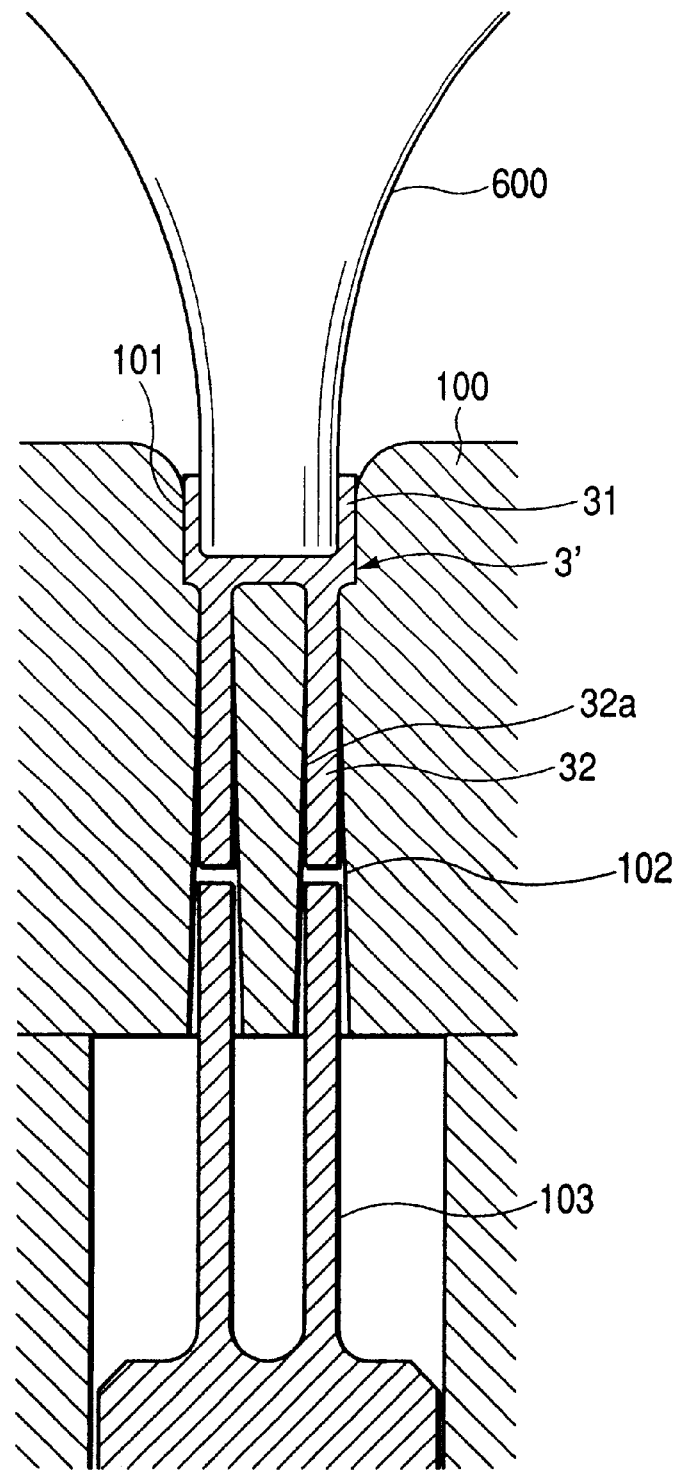
FIG. 16 is a front view showing in section a step in the process for producing a distal end support member of an endoscopic treatment tool according to the second embodiment of the invention.
Figure 17:
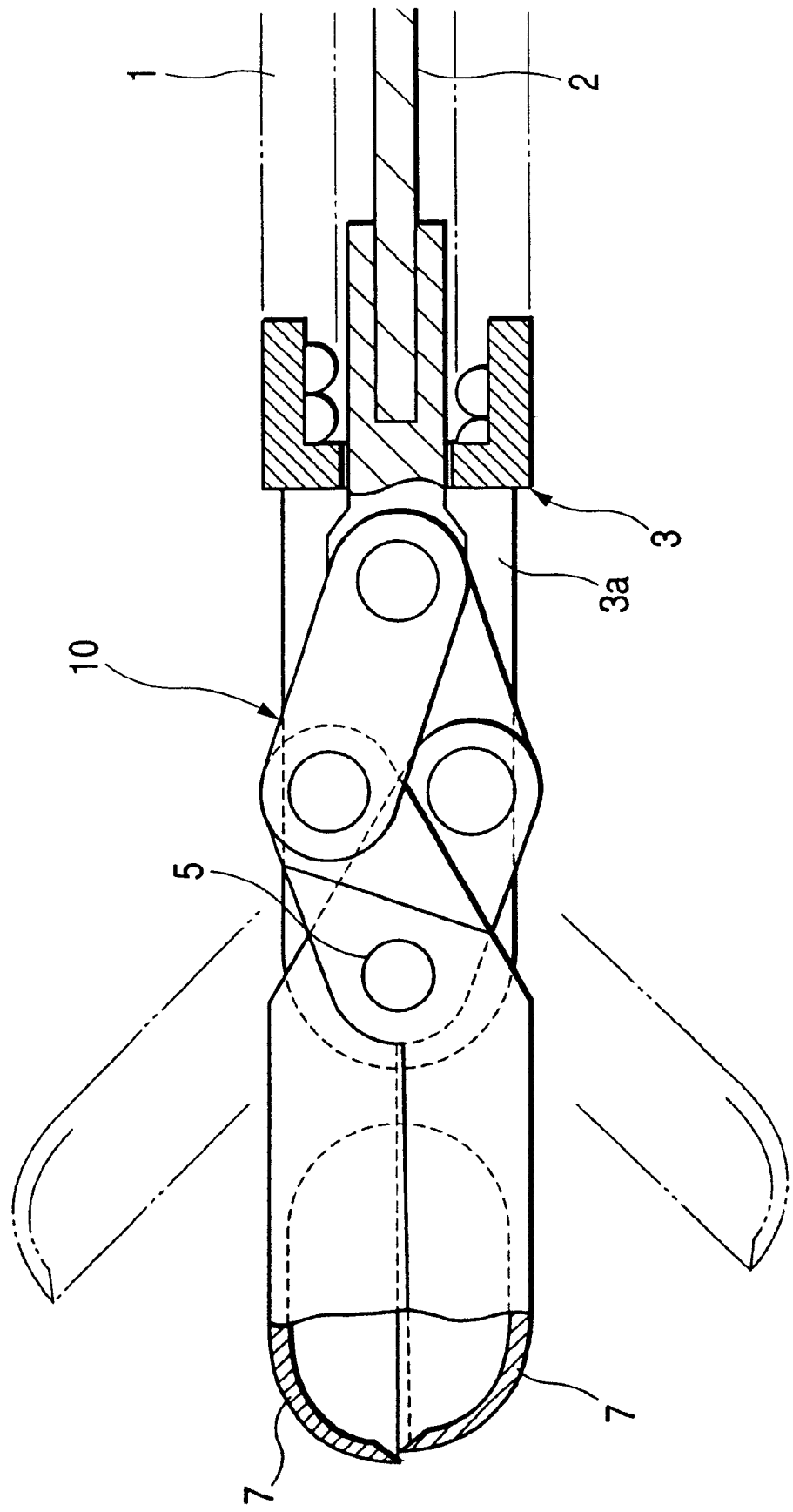
FIG. 17 is aside view showing, in partial section, the distal end portion of conventional endoscopic biopsy forceps.
Figure 18:
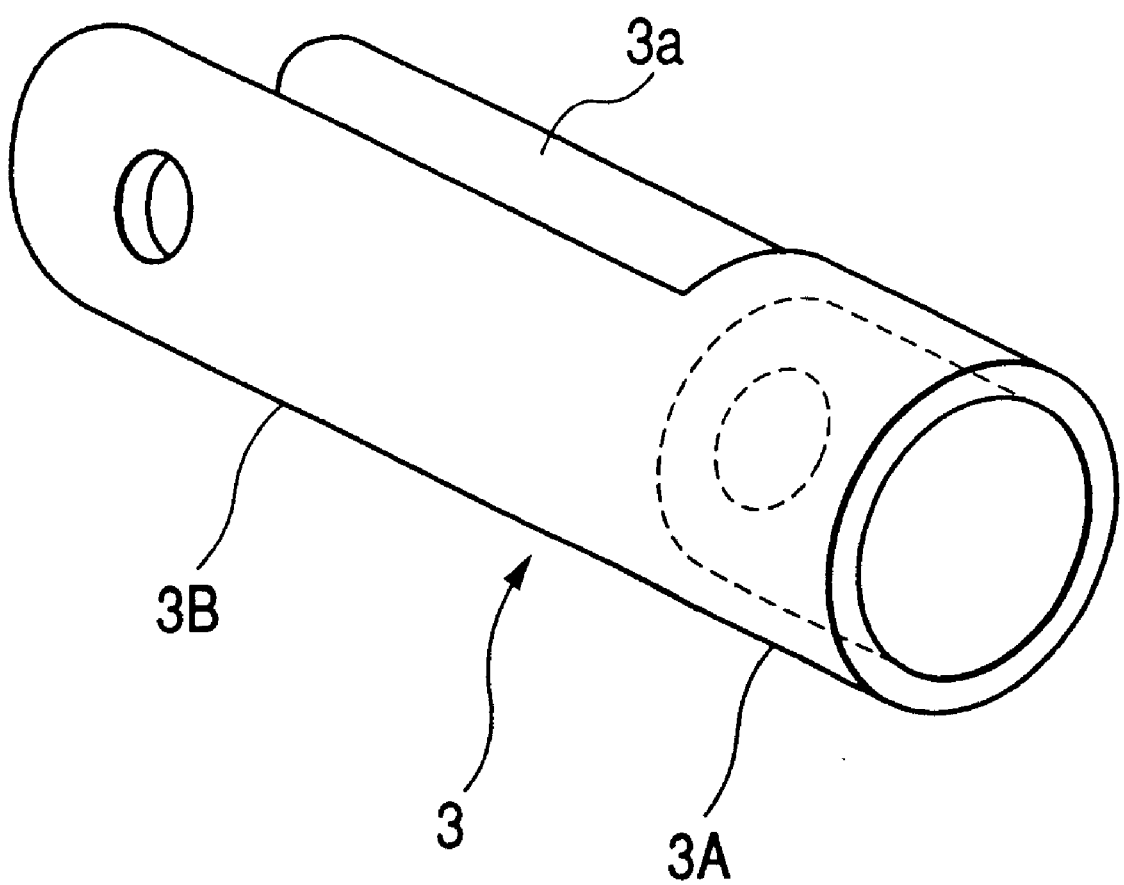
FIG. 18 is a perspective view of a conventional distal end support member.

FIG. 16 shows a step in the forging process that is employed to fabricate a distal end support member of an endoscopic treatment tool according to a second embodiment of the invention. A punch 600 whose tip diameter is made smaller than the stock receiving hole 101 in the die 100 by a difference equal to the wall thickness of the sheath coupling portion 31 is pushed into the stock 3' so that the sheath coupling portion 31 and the drive mechanism holding groove portion 32 are shaped simultaneously. This embodiment is more advantageous than the first one since it does not produce the flange portion 34 which must eventually be cut off.

It should be noted that the present invention is by no means limited to the foregoing embodiments and it may be applied to the production of parts of various endoscopic treatment tools other than biopsy forceps.

What is claimed is:

1. A process for producing a distal end support member of an endoscopic treatment tool which comprises a drive mechanism holding groove portion and a sheath coupling portion, said drive mechanism holding groove portion having a slit of gap formed to extend from its distal end so as to hold a distal end treatment member drive mechanism in a movable fashion and said sheath coupling portion being formed in an annular shape so that it can be coupled to the distal end of a sheath, wherein said drive mechanism holding groove portion is formed by forging that portion of a cylindrical metal stock which is closer to its front end such that it is extruded through a pair of extrusion die openings in a first direction along its longitudinal axis into a nonconfining space, without conforming to an interior shape of a die mold cavity, to form a slit of gap in the middle whereas said sheath coupling portion is formed by forging that portion of said metal stock which is closer to its rear end such that it is extruded in an annular shape in a second direction opposite said first direction.

2. The process according to claim 1, wherein in order to extrude said sheath coupling portion by forging, a first punch used to forge said drive mechanism holding groove portion is replaced by a second punch that defines an annular clearance from a die and which is used to perform forging in the same direction as the forging of said drive mechanism holding groove portion.

3. The process according to claim 1, wherein a punch and die that are used to forge said drive mechanism holding groove portion have an annular clearance so that when said drive mechanism holding groove portion is extruded, said sheath coupling portion is simultaneously extruded between said punch and die.

4. The process according to claim 1, wherein a through-hole that crosses said slit of gap in said drive mechanism holding groove portion and which opens on both sides of said drive mechanism holding groove portion is pierced by forging, provided that a side of said drive mechanism holding groove portion that first contacts a punch is punched to make a first hole and the resulting scrap is pushed forward until it contacts the other side of said drive mechanism holding groove portion and punches it to make a second hole.

5. A process for producing a distal end support member of an endoscopic treatment tool, the process comprising:
   (a) placing a plastically deformable material on a die having a pair of holes which each include a die opening and tapered interior walls, the material having a first side and a second side opposite from the first side;
   (b) contacting a first punch with the first side of the material, and pressurizing the material to the die using the first punch so that part of material in the second side is plastically extruded into the holes through the die openings, without being confined by the tapered interior walls of the holes, to form a pair of elongating pieces having a gap therebetween; and
   (c) contacting a second punch with the first side of the material and pressurizing the material to the die using the second punch so that part of material in the first side is extruded along an annular clearance formed between the second punch and the die.

6. The process according to claim 5, wherein the first punch is contacted with the first side of the material prior to or subsequently to contacting the second punch with the first side of the material.

7. The process according to claim 5, further comprising:
   continuously piercing distal end portions of the elongating pieces across the gap using a third punch so that a scrap obtained as a consequence of piercing one distal end portion is discharged through the other distal end portion when the other distal end portion is pierced.

8. A process for producing a distal end support member of an endoscopic treatment tool, the process comprising:
   (a) placing a plastically deformable material on a die having a pair of holes which each include a die opening and tapered interior walls, the material having a first side and a second side opposite from the first side; and
   (b) contacting a punch with the first side of the material, and pressurizing the material to the die using the punch so that part of material in the second side is plastically extruded into the holes through the die openings, without being confined by the tapered interior walls of the holes, to form a pair of elongating pieces having a gap therebetween, and so that part of material in the first side is extruded along an annular clearance formed between the punch and the die.

9. The process according to claim 8, wherein the parts of material in the first side and the second side are extruded simultaneously.

10. The process according to claimed 8, further comprising:
   continuously piercing distal end portions of the elongating pieces across the gap using another punch so that a scrap obtained as a consequence of piercing one distal end portion is discharged through the other distal end portion when the other distal end portion is pierced.

* * * * *